(12) United States Patent
Horie

(10) Patent No.: US 9,321,044 B2
(45) Date of Patent: Apr. 26, 2016

(54) CATALYST-SUPPORTING POROUS MEMBRANE, CATALYST MEMBER, AIR CLEANING DEVICE, AND METHOD FOR PRODUCING CATALYST-SUPPORTING POROUS MEMBRANE

(75) Inventor: Wataru Horie, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 120 days.

(21) Appl. No.: 13/982,767

(22) PCT Filed: Jan. 26, 2012

(86) PCT No.: PCT/JP2012/051661
§ 371 (c)(1),
(2), (4) Date: Jul. 31, 2013

(87) PCT Pub. No.: WO2012/105407
PCT Pub. Date: Aug. 9, 2012

(65) Prior Publication Data
US 2013/0315786 A1 Nov. 28, 2013

(30) Foreign Application Priority Data
Feb. 2, 2011 (JP) ................... 2011-020933

(51) Int. Cl.
*B01J 31/06* (2006.01)
*B01J 21/06* (2006.01)
(Continued)

(52) U.S. Cl.
CPC ............... *B01J 31/06* (2013.01); *A61L 9/205* (2013.01); *B01D 53/88* (2013.01); *B01D 69/145* (2013.01); *B01J 21/063* (2013.01); *B01J 23/06* (2013.01); *B01J 35/004* (2013.01); *B01J 37/0215* (2013.01); *A61L 9/16* (2013.01);
(Continued)

(58) Field of Classification Search
CPC ......... A61L 9/205; B01J 31/06; B01J 21/063; B01J 23/06; B01J 35/004; B01J 37/0215; B01D 53/88; B01D 69/145
See application file for complete search history.

(56) References Cited

U.S. PATENT DOCUMENTS

| 5,547,823 A | 8/1996 | Murasawa et al. |
| 6,277,346 B1 | 8/2001 | Murasawa et al. |

(Continued)

FOREIGN PATENT DOCUMENTS

| JP | 07171408 | 7/1995 |
| JP | 2000093809 A | 4/2000 |

(Continued)

OTHER PUBLICATIONS

International Search Report PCT/ISA/210 for International Application No. PCT/JP2012/051661 Dated on Jan. 26, 2012.

(Continued)

*Primary Examiner* — Regina M Yoo
(74) *Attorney, Agent, or Firm* — Harness, Dickey & Pierce, P.L.C.

(57) ABSTRACT

A catalyst-supporting porous film includes: a resin layer; and catalyst particles dispersed in the resin layer. The catalyst particles are unevenly distributed so as to be present at a surface of the resin layer. Preferably, the catalyst-supporting porous film includes a porous section and a supporting section for supporting the porous section. The number of catalyst particles per unit volume in the porous section is greater than the number of catalyst particles per unit volume in the supporting section. Thus, a catalyst-supporting porous film which has a high catalytic effect can be provided.

13 Claims, 6 Drawing Sheets

(51) Int. Cl.
*B01J 23/06* (2006.01)
*B01D 53/88* (2006.01)
*B01D 69/14* (2006.01)
*B01J 35/00* (2006.01)
*B01J 37/02* (2006.01)
*A61L 9/20* (2006.01)
*A61L 9/16* (2006.01)
*F24F 3/16* (2006.01)

(52) U.S. Cl.
CPC ......... *A61L 2209/14* (2013.01); *A61L 2209/15* (2013.01); *B01D 2255/20707* (2013.01); *B01D 2255/802* (2013.01); *B01D 2257/90* (2013.01); *B01D 2257/91* (2013.01); *B01D 2258/06* (2013.01); *B01D 2325/10* (2013.01); *F24F 2003/1664* (2013.01); *F24F 2003/1682* (2013.01)

(56) References Cited

U.S. PATENT DOCUMENTS

| 6,673,744 | B1* | 1/2004 | Taguchi et al. | 503/227 |
| 7,531,238 | B2* | 5/2009 | Mizuno et al. | 428/423.5 |
| 2001/0046937 | A1 | 11/2001 | Murasawa et al. | |
| 2006/0074172 | A1* | 4/2006 | Yang et al. | 524/492 |
| 2007/0013827 | A1* | 1/2007 | Fang | 349/58 |
| 2007/0141114 | A1* | 6/2007 | Muisener et al. | 424/427 |
| 2008/0131704 | A1* | 6/2008 | Mizuno et al. | 428/423.1 |
| 2009/0147196 | A1 | 6/2009 | Horie et al. | |

FOREIGN PATENT DOCUMENTS

| JP | 2001183506 A | 7/2001 |
| JP | 2004106348 A | 4/2004 |
| JP | 2007279633 A | 10/2007 |
| JP | 2009128488 A | 6/2009 |
| JP | 2009221061 A | 10/2009 |
| JP | 2009231182 A | 10/2009 |
| JP | 2010125357 A | 6/2010 |

OTHER PUBLICATIONS

International Preliminary Report on Patentability and Written Opinion dated Aug. 15, 2013.

* cited by examiner

*FIG.6*
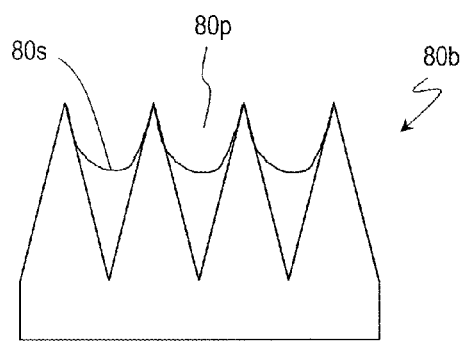
*FIG.7*
(a)
(b)
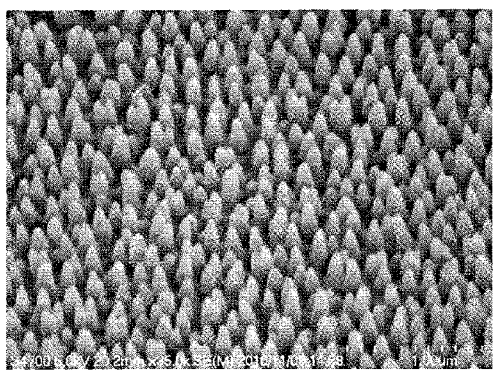
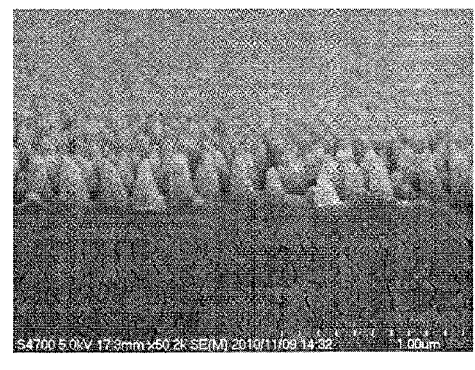

CATALYST-SUPPORTING POROUS MEMBRANE, CATALYST MEMBER, AIR CLEANING DEVICE, AND METHOD FOR PRODUCING CATALYST-SUPPORTING POROUS MEMBRANE

TECHNICAL FIELD

The present invention relates to a catalyst-supporting porous film, a catalyst member, an air cleaning device, and a catalyst-supporting porous film manufacturing method.

BACKGROUND ART

Photocatalysts are capable of decomposition of organic substances and hydrophilization of a film surface and have been employed for uses including surface cleaning, deodorization, antimicrobial treatments, etc. Usually, catalyst particles, such as titanium oxide particles, are dispersed in a dispersion, and this dispersion is applied over a base and dried, whereby a film which has catalyst particles supported thereon is formed. In general, the catalytic effect increases according to the surface area of this film. Therefore, forming a catalyst-supporting film such that the surface of the film has an uneven structure has been considered (see Patent Documents 1 to 4).

Patent Document 1 discloses that a coating agent, which is a mixture of photocatalyst particles and a binder resin, is applied over a base which has a surface with minute unevenness so as to form a coating layer over the surface of the base. However, applying the coating agent over the uneven surface of the base in such a way leads to that the catalyst particles are caught in recessed portions so that the catalytic effects would not efficiently increase in some cases.

On the other hand, Patent Documents 2 to 4 disclose that a mixture (dispersion) is applied over a surface of a base, and thereafter, a surface of the mixture is deformed so as to have an uneven structure. Specifically, Patent Document 2 discloses forming an uneven structure which has a cleaning function and an antireflection function over a lens. Patent Document 3 discloses using a porous alumina layer formed by anodization as a mold so as to form a minute uneven pattern in an inorganic material which has a photocatalytic property. Patent Document 4 discloses a photocatalytic layer which has a moth-eye structure in order to realize a low reflection property. In this way, a surface of a film which has catalyst particles supported thereon is deformed into a porous shape, whereby the catalytic action can be increased.

CITATION LIST

Patent Literature

Patent Document 1: Japanese Laid-Open Patent Publication No. 2010-125357
Patent Document 2: Japanese Laid-Open Patent Publication No. 2007-279633
Patent Document 3: Japanese Laid-Open Patent Publication No. 2009-221061
Patent Document 4: Japanese Laid-Open Patent Publication No. 2001-183506

SUMMARY OF INVENTION

Technical Problem

The catalyst-supporting films of Patent Documents 1 to 4 have relatively large surface areas and exhibit relatively high catalytic effects. However, in order to further increase the catalytic effect, it is necessary to increase the number of catalyst particles which are present in the vicinity of the surface of the catalyst-supporting film rather than increasing the surface area of the catalyst-supporting film. However, simply increasing the number of catalyst particles dispersed in the dispersion for the purpose of increasing the number of catalyst particles leads to reduction in adhesion between the catalyst particles, so that the catalyst-supporting film can be fragile.

The present invention was conceived in view of the above problems. One of the objects of the present invention is to provide a catalyst-supporting porous film which has a high catalytic effect, a catalyst member, an air cleaning device, and a catalyst-supporting porous film manufacturing method.

Solution to Problem

A catalyst-supporting porous film of the present invention includes: a resin layer; and catalyst particles dispersed in the resin layer, wherein the catalyst particles are unevenly distributed so as to be present at a surface of the resin layer.

In one embodiment, the catalyst-supporting porous film includes a porous section and a supporting section for supporting the porous section, and the number of catalyst particles per unit volume in the porous section is greater than the number of catalyst particles per unit volume in the supporting section.

In one embodiment, the catalyst-supporting porous film has a surface of a moth-eye structure or inverted moth-eye structure.

In one embodiment, the surface has a plurality of minute raised portions and a saddle portion extending between vertexes of adjacent two of the plurality of minute raised portions.

In one embodiment, the resin layer contains a photocurable resin.

In one embodiment, the resin layer contains a plurality of thermoplastic resins which are phase-separated from one another.

In one embodiment, the catalyst particles include titanium oxide particles.

In one embodiment, the catalyst particles include zinc-supporting titanium oxide particles.

In one embodiment, a through hole is provided.

A catalyst member of the present invention includes: a base which has a principal surface; and a catalyst-supporting porous film provided on the principal surface of the base.

A catalyst member of the present invention includes: a base which has two principal surfaces; and a catalyst-supporting porous film provided on each of the two principal surfaces of the base.

An air cleaning device of the present invention includes: the above-described catalyst-supporting porous film; and an ion generating device for generating a positive ion and a negative ion.

A catalyst-supporting porous film manufacturing method of the present invention includes the steps of: providing a mixture which contains catalyst particles, a resin, and a solvent; applying the mixture on a base and drying the mixture; and deforming a surface of the dried mixture into a porous shape, wherein the step of drying includes forming a resin layer from the mixture, in which the catalyst particles being dispersed, and the catalyst particles are unevenly distributed so as to be present at a surface of the resin layer.

In one embodiment, in the step of providing, the resin contains a photocurable resin, and the step of deforming into the porous shape further includes curing the photocurable resin with a mold being pressed against the mixture.

In one embodiment, in the step of curing, the mold has a surface of a moth-eye structure or inverted moth-eye structure.

Advantageous Effects of Invention

According to the present invention, a catalyst-supporting porous film which has a high catalytic effect, a catalyst member, an air cleaning device, and a catalyst-supporting porous film manufacturing method can be provided.

BRIEF DESCRIPTION OF DRAWINGS

FIG. 6 A schematic diagram of an alternative mold which is for use in the catalyst-supporting porous film manufacturing method.

FIG. 7 Electron microscopic images of an embodiment of the catalyst-supporting porous film of the present invention. (a) is a bird's-eye view. (b) is a cross-sectional view.

DESCRIPTION OF EMBODIMENTS

Figure 1:
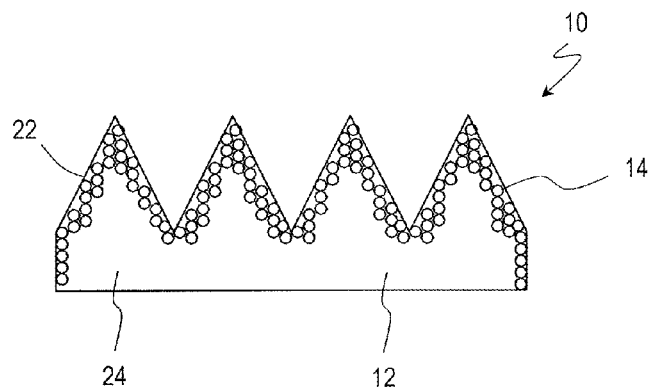
FIG. 1 A schematic diagram of an embodiment of a catalyst-supporting porous film of the present invention.

Hereinafter, embodiments of a catalyst-supporting porous film, a catalyst member, an air cleaning device, and a catalyst-supporting porous film manufacturing method of the present invention are described with reference to the drawings. Note that, however, the present invention is not limited to the embodiments which will be described below.

An embodiment of a catalyst-supporting porous film of the present invention is described with reference to FIG. 1. The catalyst-supporting porous film 10 of the present embodiment includes a resin layer 12 and catalyst particles dispersed in the resin layer 12. For example, the catalyst particles 14 are titanium oxide particles, zinc-supporting titanium oxide particles, silver-supporting titanium oxide particles, or silver-supporting silicon dioxide aluminum oxide particles. These are commercially available as Atomy Ball from JGC Catalysts and Chemicals Ltd. These particles are sometimes generically referred to as "inorganic oxide microparticles" or "metal catalyst-supporting inorganic oxide microparticles".

In the catalyst-supporting porous film 10 of the present embodiment, the catalyst particles 14 are unevenly distributed so as to be present at the surface of the resin layer 12. For example, almost all of the surface of the resin layer 12 is covered with the catalyst particles 14. Since the catalyst-supporting porous film 10 including the catalyst particles 14 is a porous film which has a relatively large surface area and the catalyst particles 14 are unevenly distributed so as to be present at the surface of the resin layer 12, the catalytic effect can be efficiently increased. Note that, in this specification, the catalyst-supporting porous film 10 is sometimes simply referred to as "catalyst-supporting film 10" or "film 10".

The catalyst-supporting film 10 includes a porous section 22 which has a porous shape and a supporting section 24 for supporting the porous section 22. Here, a plurality of raised portions are defined by the porous shape of the porous section 22. The raised portions have a conical shape or a bell-like shape. Such a structure is also referred to as "moth-eye structure".

Although its size is not precisely shown in FIG. 1, the thickness of the porous section 22 is smaller than that of the supporting section 24, and the porous section 22 that has a minute shape is provided over the supporting section 24 that has a greater thickness. For example, the thickness of the porous section 22 is about 200 nm, and the thickness of the supporting section 24 is about 10 μm. In the catalyst-supporting film 10 of the present embodiment, the number of catalyst particles 14 per unit volume in the porous section 22 is greater than the number of catalyst particles 14 per unit volume in the supporting section 24, so that the catalytic effect is efficiently increased. Note that the number of catalyst particles 14 per unit volume can be measured using a transmission electron microscope (TEM).

For example, when the catalyst particles 14 are titanium oxide particles, the catalyst-supporting film 10 exhibits relatively strong oxidizing effect and hydrophilic effect. On the other hand, when the catalyst particles 14 are zinc-supporting titanium oxide particles, the catalyst-supporting film 10 exhibits slightly low oxidizing effect and hydrophilic effect as compared with the case where the catalyst particles 14 are titanium oxide particles. Note that, however, slightly reducing the oxidizing effect of the catalyst particles 14 enables to prevent deterioration and discoloration of the resin layer 12 in which the catalyst particles 14 are dispersed. When the catalyst particles 14 are zinc-supporting titanium oxide particles, the catalyst-supporting film 10 exhibits an oxidizing effect to some extent even if the catalyst-supporting film 10 is not irradiated with light. Therefore, decomposition and deodorization of organic substances can be achieved.

The resin layer 12 may be made of an inorganic resin or may be made of an organic resin. When the catalyst particles 14 are photocatalyst particles (for example, titanium oxide particles), from the viewpoint of preventing decomposition of the resin layer 12 by the catalyst particles 14, the resin layer 12 is preferably made of an inorganic resin. From the viewpoint of retention of the catalyst particles 14 and durability of the catalyst-supporting film 10, the resin layer 12 is preferably made of an organic resin. Alternatively, for example, the resin layer 12 may be made of a fluoric resin. When the catalyst particles 14 are zinc-supporting titanium oxide particles, decomposition of the resin layer 12 by the catalyst particles 14 is relatively unlikely to occur. Therefore, the resin layer 12 is preferably made of an organic resin.

Figure 2:
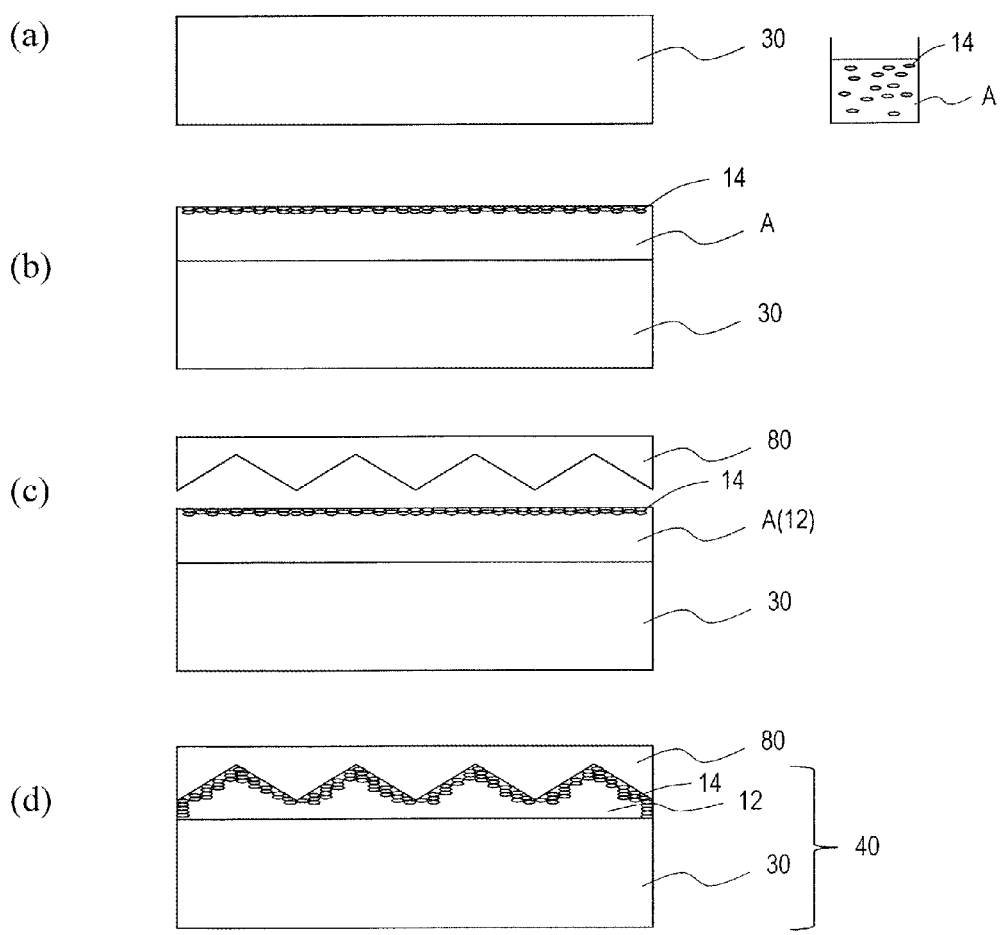
FIG. 2 (a) to (d) are schematic diagrams for illustrating an embodiment of a catalyst-supporting porous film manufacturing method of the present invention.

Hereinafter, a method for manufacturing the catalyst-supporting film 10 of the present embodiment is described with reference to FIG. 2.

First, as shown in FIG. 2(a), a mixture A and a base 30 are provided. The mixture A contains the catalyst particles 14, a resin, and a solvent. The solvent used may be an alcohol solvent, for example. Alternatively, the solvent used may be a ketone solvent or may be a mixture of an alcohol solvent and a ketone solvent.

For example, the catalyst particles 14 are titanium oxide particles. Alternatively, the catalyst particles 14 used may be zinc-supporting titanium oxide particles. For example, the zinc-supporting titanium oxide particles used may be Atomy Ball TZ-R available from JGC Catalysts and Chemicals Ltd. Atomy Ball TZ-R contains zinc and titanium oxide and has average particle diameter of about 10 nm. The catalyst particles 14 may be provided with a surface treatment. For example, the surface treatment may be carried out using a coupling agent, such as a silane coupling agent.

In general, the surface of inorganic oxide microparticles or metal catalyst-supporting inorganic oxide microparticles that constitute the catalyst particles 14 is hydrophilic. The degree of the hydrophilicity of the catalyst particles 14 can be modified by a surface treatment. The resin preferably contains a resin whose hydrophilicity is higher than that of the catalyst particles 14.

The resin may contain a curable resin or may contain a thermoplastic resin. The curable resin may be a thermosetting resin or may be a photocurable resin. The curable resin advantageously has high hardness and high mechanical strength. The photocurable resin (including UV-curable resins and electron beam curable resins) advantageously has a fast curing speed. The resins which may be used in the embodiments of the present invention are disclosed in Japanese Laid-Open Patent Publication No. 2009-128488, for example. The entire disclosures of Japanese Laid-Open Patent Publication No. 2009-128488 are incorporated by reference in this specification.

Examples of the thermoplastic resin include styrene resins, (meth)acrylic resins, organic acid vinyl ester resins, vinyl ether resins, halogen-containing resins, olefin resins (including alicyclic olefin resins), polycarbonate resins, polyester resins, polyamide resins, thermoplastic polyurethane resins, polysulfone resins (polyethersulfones, polysulfones, and the like), polyphenylene ether resins (2,6-xylenol polymers, and the like), cellulose derivatives (cellulose esters, cellulose carbamates, cellulose ethers, and the like), silicone resins (polydimethyl siloxanes, polymethyl phenyl siloxanes, and the like), and rubbers or elastomers (diene rubbers such as polybutadienes, polyisoprenes, and the like, styrene-butadiene copolymers, acrylonitrile-butadiene copolymers, acrylic rubbers, urethane rubbers, silicone rubbers, etc.). These thermoplastic resins may be used solely, or two or more of them may be used in combination.

Examples of the thermosetting resin include epoxy resins, unsaturated polyester resins, urethane resins and silicone resins which have an epoxy group, an isocyanate group, an alkoxysilyl group, a silanol group, a polymeric group (such as a vinyl group, an allyl group, a (meth)acryloyl group), or the like.

The photocurable resin used may be selected from a wide variety of monomers and oligomers which are curable by an active light ray (ultraviolet ray, visible ray, electron beam, etc.). The photocurable resin may be, for example, a monomer and/or oligomer which has a vinyl group, an allyl group, a (meth)acryloyl group, or a photosensitive group (such as a cinnamoyl group). For example, an acrylic or methacrylic monomer and/or oligomer may be suitably used. The monomer or oligomer may be monofunctional or may be polyfunctional (i.e., may have 2 to 6 polymeric groups). A monomer and an oligomer may be appropriately mixed. Alternatively, a monofunctional monomer or oligomer and a polyfunctional monomer or oligomer may be mixed. Further, when necessary, an initiator, a polymerization promoter, and/or a polymerization inhibitor may be mixed.

The base 30 may be a glass substrate. Alternatively, the base 30 may be a film which is made of triacetyl cellulose (TAC), acryl or polyethylene terephthalate (PET).

Then, as shown in FIG. 2(b), the mixture A is applied over the base 30, and the mixture A is dried. For example, the thickness of the applied mixture A is about 10 μm. Here, the mixture A is applied over one of the principal surfaces of the base 30. The temperature during the drying is preferably set to a temperature which is lower than the boiling point of the solvent. After the application, it may be left at normal temperature or room temperature for a while (e.g., about one minute) and then dried using a drier. Alternatively, the drying may be carried out while applying a predetermined amount of air flow.

During the drying, the solvent contained in the mixture is vaporized, whereby the resin layer 12 is formed in which the catalyst particles 14 are dispersed. Although details will be described later, the catalyst particles 14 inside the mixture A move to the surface of the mixture A with the progress of the drying, so that the catalyst particles 14 are unevenly distributed so as to be present at the surface of the resin layer 12. Note that, as a result of the drying, an uneven structure may be formed in the surface of the resin layer 12.

Then, as shown in FIG. 2(c), a mold 80 is pressed against the mixture A so as to deform the surface of the mixture A into a porous shape. For example, the mold 80 may have a surface of a moth-eye structure or inverted moth-eye structure. Although details will be described later, the mold 80 which has a surface of an inverted moth-eye structure can be formed by repeatedly performing anodization and etching on an aluminum base.

Thereafter, as shown in FIG. 2(d), the photocurable resin is cured. In the case where the base 30 has relatively high light transmittance, light for irradiation may be supplied such that the light is transmitted through the base 30. Thereafter, the mold 80 is peeled away from the catalyst-supporting film 10. When necessary, the catalyst-supporting film 10 may be peeled away from the base 30. Alternatively, a member 40 which includes the catalyst-supporting film 10 and the base 30 may be used as the catalyst member. Thus, the catalyst-supporting film 10 can be manufactured as described hereinabove.

When the catalyst-supporting film 10 has a surface of a moth-eye structure, the surface area S of the catalyst-supporting film 10 is expressed as shown below. Here, a moth-eye structure is assumed in which circular cones with radius r and height h are arranged in a close-packed arrangement on a square supporting section with length x on each side.

$$S = x^2 + (\text{int}(x/(2r)))^2 \times (\pi r (r^2+h^2)^{1/2} - \pi r^2)$$

where int( ) represents the integer part of the number in the parentheses.

Figure 3:
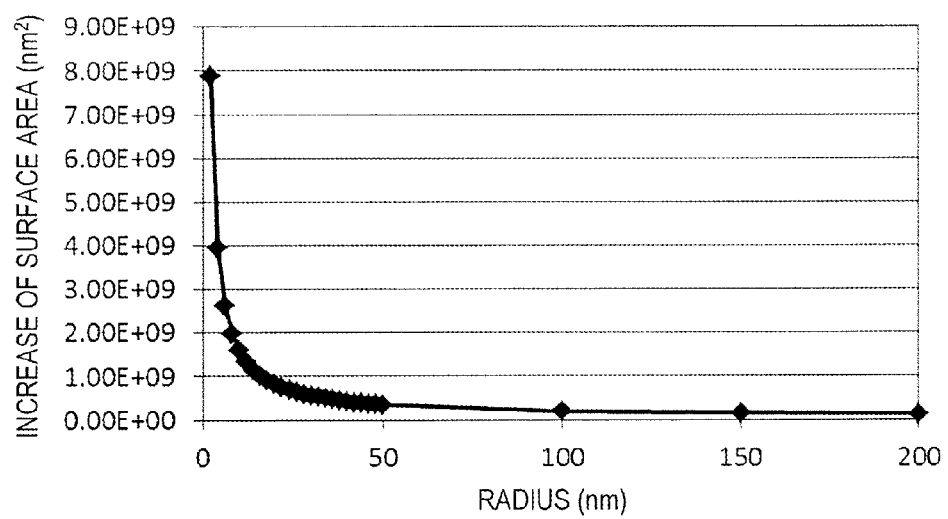
FIG. 3 A graph showing a variation of the surface area with respect to the radius.

FIG. 3 shows a variation of the surface area with respect to a variation of the radius of the circular cones. Here, the height h of the circular cones is constant at 100 nm. As understood from FIG. 3, the surface area of the catalyst-supporting film 10 increases as the radius of the circular cones decreases. Preferably, the radius of the circular cones is not more than 100 nm. More preferably, the radius of the circular cones is not more than 50 nm.

Figure 4:
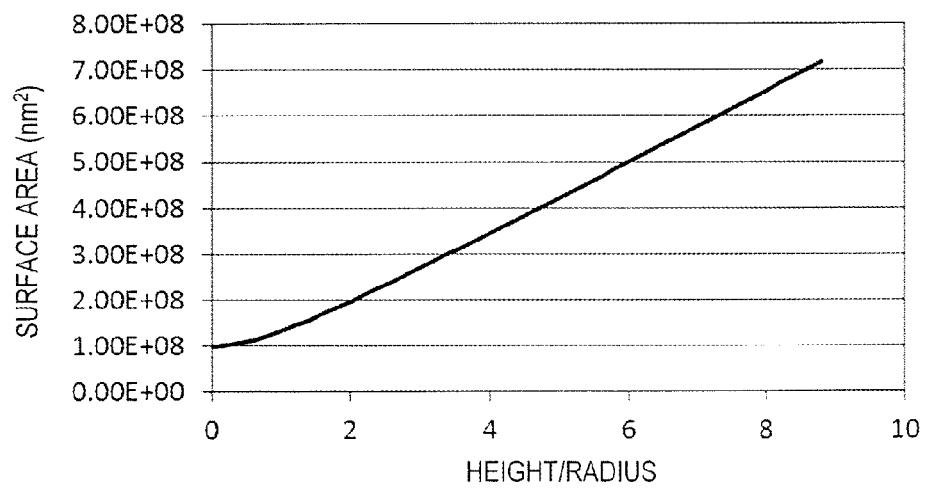
FIG. 4 A graph showing a variation of the surface area with respect to the aspect ratio (height/radius).

FIG. 4 shows a variation of the surface area with respect to a variation of the aspect ratio (height/radius) of the circular cones. Here, the radius r is constant at 100 nm. As understood from FIG. 4, the surface area increases as the aspect ratio (height h/radius r) of the circular cones increases.

The mold 80 is suitably manufactured using a porous alumina layer. Hereinafter, an example of the method for manufacturing the mold 80 is described with reference to FIG. 5.

Figure 5:
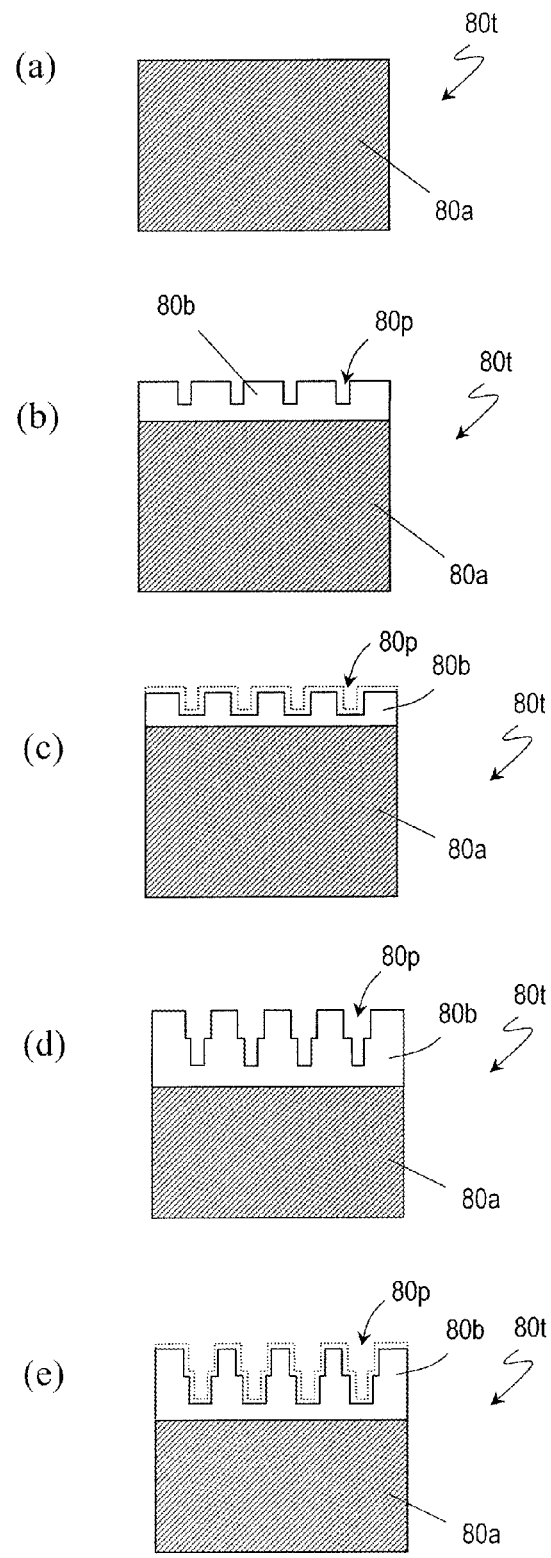
FIG. 5 (a) to (e) are schematic diagrams for illustrating a manufacturing method of a mold which is for use in the catalyst-supporting porous film manufacturing method.

First, as shown in FIG. 5(*a*), a mold base 80*t* is provided which has an aluminum film 80*a* over its surface. The mold base 80*t* may include a support (not shown) and an aluminum film 80*a* provided on the support. Alternatively, the mold base 80*t* may be an aluminum base.

Then, the aluminum film 80*a* is anodized so as to form a porous alumina layer 80*b* which has micropores 80*p* extending perpendicular to the surface of the aluminum film 80*a* as shown in FIG. 5(*b*). By the anodization, oxidation and dissolution of the aluminum film 80*a* concurrently advance so that the micropores 80*p* extending perpendicular to the surface of the aluminum film 80*a* are formed.

For example, the anodization may be realized by immersing a base in an acidic electrolytic solution of sulfuric acid, oxalic acid, phosphoric acid, or the like, or an alkaline electrolytic solution, and applying a voltage with the base being used as an anode. In this process, the average distance between the centers of adjacent micropores and the depth of the micropores vary depending on the conditions of the anodization. Note that the average distance between the centers of adjacent micropores is approximately twice the thickness of a barrier layer, and is approximately proportional to the voltage that is applied during the anodization. The pore diameter of the micropores depends on the type, concentration, temperature, etc., of the electrolytic solution. The micropores are preferably arranged with a regularity degraded to some extent. Note that, however, the micropores may be in an irregular (i.e., non-periodic) arrangement or may be in a regular arrangement.

For example, in the case where the average distance between the centers of adjacent micropores 80*p* is about 180 nm, the anodization is performed for 25 seconds with the forming voltage of 80 V using an electrolytic solution of 0.6 wt % oxalic acid at the solution temperature of 5° C. In the case where this average distance is 400 nm, the anodization is performed for 30 to 45 seconds with the forming voltage of 200 V using an electrolytic solution of 2 wt % tartaric acid at the solution temperature of 5° C.

Then, the etching is performed, whereby the pore diameter of the micropores 80*p* is increased as shown in FIG. 5(*c*). For example, the etching may be performed for several tens of minutes using 1 mol/L phosphoric acid at the solution temperature of 30° C.

Then, the aluminum film 80*a* is again partially anodized such that the micropores 80*p* are grown in the depth direction and the thickness of the porous alumina layer 80*b* is increased as shown in FIG. 5(*d*). Here, the growth of the micropores 80*p* starts at the bottom of the previously-formed micropores 80*p*, so that the lateral surface of the micropores 80*p* has a stepped shape.

Thereafter, when necessary, the porous alumina layer 80*b* is further etched such that the pore diameter of the micropores 80*p* is further increased as shown in FIG. 5(*e*). The etching is performed in the same way as the above-described etching. The thus-formed porous alumina layer 80*b* is used as the mold 80. Note that the mold 80 may have a shape of a solid circular cylinder or hollow circular cylinder.

To further increase the surface area of the porous alumina layer 80*b*, the aluminum film 80*a* may contain at least one impurity element selected from the group consisting of Fe, Si, Cu, Mn, Zn, Ti, Pb, Sn, and Mg. In this case, recessed portions which are difference from the micropores 80*p* are formed during the first etching cycle, so that the surface area of the porous alumina layer 80*b* can be further increased. Alternatively, recessed portions whose pore diameter is greater than that of the micropores 80*p* may be formed by carrying out the first etching cycle with an aluminum film being in contact with an electrode which contains a metal whose standard electrode potential is higher than that of the aluminum film.

In the above description, the porous alumina layer 80*b* itself is used as the mold 80, although the present invention is not limited to this example. The mold 80 may be manufactured by transfer of the porous alumina layer 80*b*. For example, the porous alumina layer 80*b* is transferred to a photocurable resin so as to form a mold which has a surface of a moth-eye structure, and this mold may be used as the mold 80 shown in FIG. 2(*c*).

In the above description, the porous section 22 has raised portions which have a conical shape or a bell-like shape, although the present invention is not limited to this example. The porous section 22 may have raised portions which have a shape of a generally circular cylinder. In the above description which has previously provided with reference to FIG. 5, both the anodization and the etching are performed alternately, although the present invention is not limited to this example. The etching may be omitted. For example, the steps shown in FIGS. 5(*c*) to 5(*e*) may be omitted.

As described above, in applying and drying of the mixture A, the catalyst particles 14 move such that they are unevenly distributed so as to be present at the surface of the resin layer 12. Possible reasons that the catalyst particles 14 are unevenly distributed so as to be present at the surface of the resin layer 12 are: the surface free energy of the catalyst particles 14; the affinity of the catalyst particles 14 for the solvent; the incompatibility of the catalyst particles 14 with the resin; and phase separation of the thermoplastic resin. For example, when the surface free energy of the catalyst particles 14 is lower than those of the other constituents in the mixture, the catalyst particles 14 move from the inner part of the mixture toward the surface. When the catalyst particles 14 have affinity for the solvent in the mixture, the catalyst particles 14 move from the inner part of the mixture toward the surface along with evaporation of the solvent from the mixture. When the catalyst particles 14 exhibit incompatibility with the resin in the mixture, the catalyst particles 14 are forced to move from the inner part of the mixture toward the surface along with reduction of the content of the solvent in the mixture through drying, and forced movement of the catalyst particles 14 from the inner part of the mixture toward the surface is further enhanced by progress of phase separation of the thermoplastic resin.

As described above, a plurality of resins may be phase-separated. After application of the mixture, when cellular rotating convection occurs in the mixture during drying, a regular or periodic uneven shape is formed in the surface of the mixture. In general, the rotating convection occurs when a portion of the mixture near the surface is cooled by evaporation heat along with evaporation of the solvent and drying, and as a result, a temperature difference is caused between the upper part and the lower part of the mixture. Such convection is also called "Benard convection" or "Rayleigh-Benard convection". In the convection which occurs in such a way, an upward movement and a downward movement are regularly repeated, and a regular or periodic uneven shape is arranged in the shape of cells across the mixture surface. The type of cellular rotating convection is not particularly limited but may be a different type of convection. For example, it may be Marangoni convection (density difference convection) which is attributed to a nonuniform distribution of the surface tension.

For example, in a mixture containing resin components which have phase separation properties from one another, these components may be allowed to undergo phase separation, whereby the catalyst particles 14 are moved. Detailed mechanisms of convection and phase separation are not yet explicated but can be inferred as described below.

In the case where convection is caused in the mixture which contains a plurality of phase-separated resins, firstly, convection cells occur after application. Then, phase separation occurs in each of the convection cells, so that the structure of the phase separation gigantically increases with the passage of time, and thereafter, growth of the phase separation stops at the cell wall of convection. As a result, an uneven shape is formed whose shape and height are controlled so as to have intervals according to the size and arrangement of the convection cells and controlled according to the phase separation structure. That is, a mixture is obtained whose shape, arrangement, and size are all controlled. It is thus inferred that, for the above reasons, the catalyst particles 14 are unevenly distributed so as to be present at the surface of the mixture A.

In the above description, in the case where anodization and etching are repeated to form the porous alumina layer 80b, the anodization and the etching may be repeatedly performed through a plurality of cycles till adjacent pores are partially connected to each other.

FIG. 6 shows a schematic diagram of the porous alumina layer 80b. The porous alumina layer 80b has a surface of an inverted moth-eye structure. The surface of the porous alumina layer 80b has a plurality of pores. These pores define a plurality of raised portions and a plurality of ridges extending between the plurality of raised portions via saddle portions 80s. For example, each of the pores has a tapered shape. Each of the raised portions has a pointed end. Each of the raised portions is surrounded by at least three pores.

In this porous alumina layer 80b, adjacent pores are partially connected to each other. The average distance between the centers of adjacent pores is generally equal to the average value of the pore diameters of the pores. Note that, strictly speaking, the distance between the centers of adjacent pores is not constant, but the difference in distance between the centers of any two adjacent pores is relatively small.

This porous alumina layer 80b is formed by repeatedly performing anodization and etching through a plurality of cycles till adjacent pores are partially connected to each other. The thus-formed porous alumina layer 80b is used as the mold 80 (FIG. 2(c)) to manufacture the catalyst-supporting film 10, whereby the surface area of the catalyst-supporting film 10 can be further increased. Thus, the catalytic effect can be further increased.

Hereinafter, an example of the catalyst-supporting film 10 is described.

Here, the catalyst particles 14 used were inorganic oxide microparticles containing a crystalline titanium oxide and silica, on which zinc was supported. As these inorganic oxide microparticles, Atomy Ball (20NZT-AC) available from JGC Catalysts and Chemicals Ltd. was used. When the inorganic oxide microparticles containing a crystalline titanium oxide and silica are used, the dispersibility of the inorganic oxide microparticles is improved, and the stability of the mixture (dispersion) A is improved, while the adhesive property of a resultant film for the base is improved, as compared with a case where inorganic oxide microparticles containing only a crystalline titanium oxide are used.

These catalyst particles 14 were added to an acrylic resin. The inorganic oxide microparticles were 10 weight % with respect to the acrylic resin. This mixture A was applied to the base 30. The base 30 was a PET film.

As the mold 80, a porous alumina layer was provided which was formed by repeatedly performing anodization and etching on an aluminum film. The mixture A was irradiated with ultraviolet light from the base 30 side with the mold 80 being pressed against the mixture A. Thereafter, the mold 80 was separated from the base 30. The thus-formed catalyst-supporting film 10 provided on the base 30 was observed using a scanning electron microscope (SEM). The surface area of a region of the resin layer 12 which was not pressed with the mold (corresponding to FIG. 2(b)) and the surface area of the other region which was pressed with the mold (corresponding to FIG. 2(c)), each of which was the area of 4.8 μm×3.3 μm, were compared with each other using the SEM. The surface area of the region which was pressed with the mold was increased about 5.1 times.

FIG. 7(a) is a bird's-eye view of an electron microscopic image of the catalyst-supporting film 10 provided on the base 30. FIG. 7(b) is a cross-sectional view of an electron microscopic image. The catalyst-supporting film 10 had a plurality of raised portions. The height of the raised portions was about 280 nm. The pitch of the raised portions was about 300 nm.

Further, the catalyst-supporting film 10 was placed over a glass plate such that the porous surface of the catalyst-supporting film 10 was exposed, and subjected to a light stability test. The test apparatus used was Super Xenon manufactured by Suga Test Instruments Co., Ltd. The irradiation condition was 60 W/m² (wavelength: 300 nm to 400 nm). The irradiation duration was 250 hours. As a result, it was confirmed that there was substantially no deterioration in the catalyst-supporting film 10, and the catalyst-supporting film 10 can endure practical use.

In the above description, the porous section 22 of the catalyst-supporting film 10 has raised portions, and the supporting section 24 is continuous, but the present invention is not limited to this example. The supporting section 24 of the catalyst-supporting film 10 may have through holes.

Figure 8:
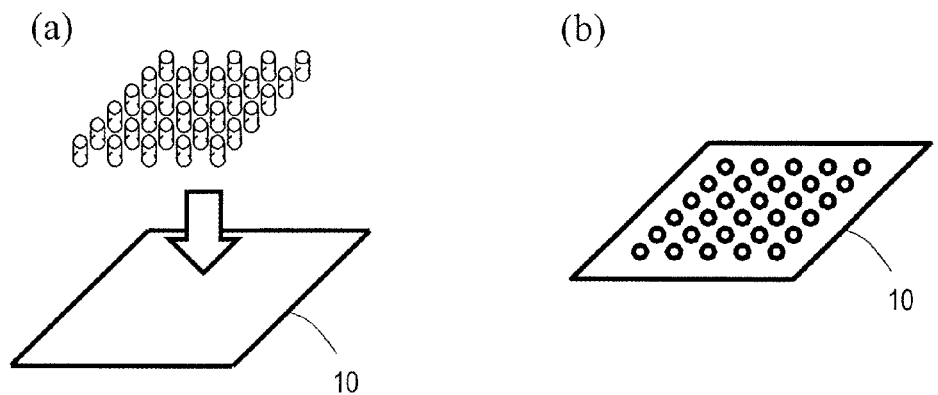
FIGS. 8 (a) and (b) are schematic diagrams of another embodiment of a catalyst-supporting porous film of the present invention.

The catalyst-supporting film 10 may be punched using a punching device which has a plurality of circular blades in a matrix arrangement as shown in FIG. 8(a), whereby the catalyst-supporting film 10 which has through holes is manufactured as shown in FIG. 8(b). For example, the diameter of the holes is preferably not less than 0.1 mm. The thus-manufactured catalyst-supporting film 10 which has through holes is suitably used as a filter.

In the above description, the catalyst-supporting film 10 is provided on one of the two principal surfaces of the base 30, but the present invention is not limited to this example. The catalyst-supporting film 10 may be provided on each of the two principal surfaces of the base 30. In this case, using a relatively thin film, such as TAC, acrylic film, PET, or the like, as the base 30 is preferred.

Figure 9:
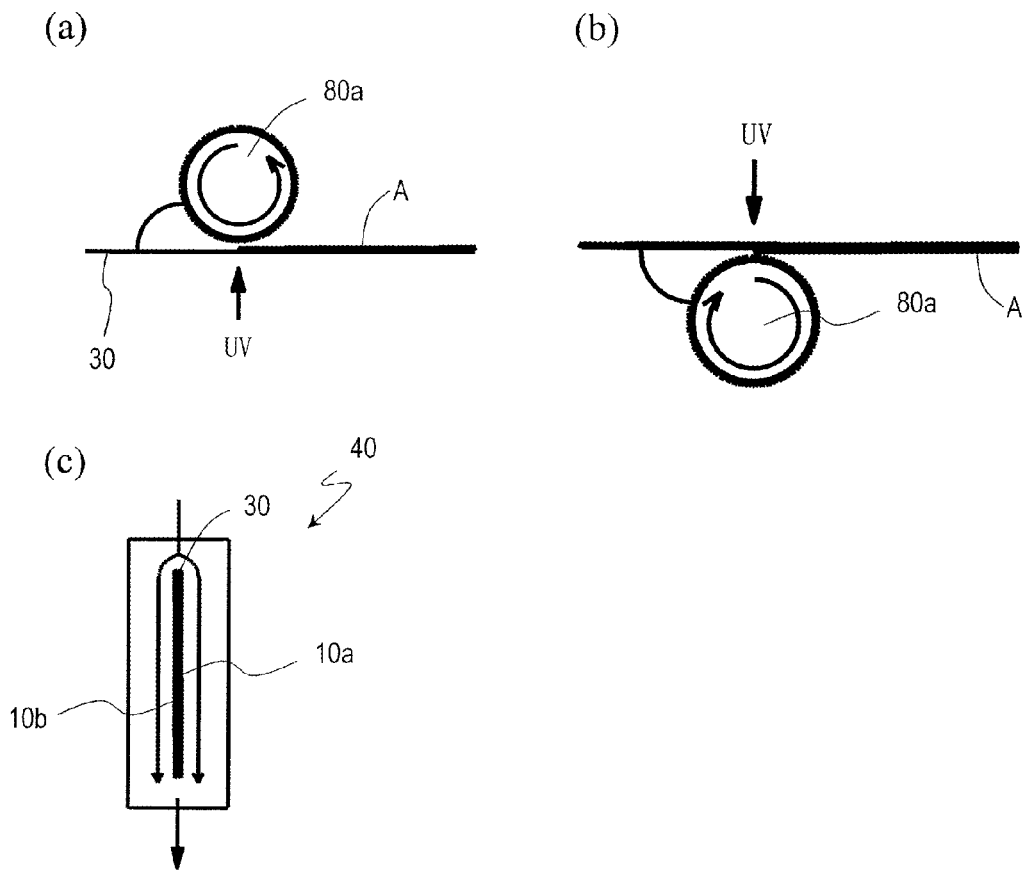
FIG. 9 (a) to (c) are schematic diagrams of an embodiment of a catalyst member which includes the catalyst-supporting porous film of the present invention.

As shown in FIG. 9(a), the mixture A is deposited on one side of the base 30 that is to be carried, and the mixture A is irradiated with ultraviolet (UV) light from the opposite side of the base 30 with a mold 80a which is in a shape of a circular solid cylinder being pressed against the mixture A. Then, as shown in FIG. 9(b), the mixture A is deposited on the opposite side surface of the base 30, and the mixture A is irradiated with ultraviolet light from the opposite side of the base 30 with a mold 80a which is in a shape of a circular solid cylinder being pressed against the mixture A. In this way, minute uneven structures are formed on both sides of the base 30.

Catalyst-supporting films 10a, 10b may be formed on both sides of the thus-obtained base 30. Note that, in the case where a catalyst base 40 in which catalyst-supporting films 10a, 10b are provided on respective ones of the two principal surfaces of the base 30 is used for air cleaning (deodorization and decomposition of organic substances), arranging the catalyst base 40 so as to be parallel to the airflow direction as shown in FIG. 9(c) enables efficient air cleaning.

In recent years, air cleaning devices which utilize ions have been used in many places. However, such air cleaning devices can deactivate viruses and molds but cannot deactivate pollens which are greater than viruses and molds. The catalyst-supporting film 10 is also suitably used for air cleaning devices.

Figure 10:
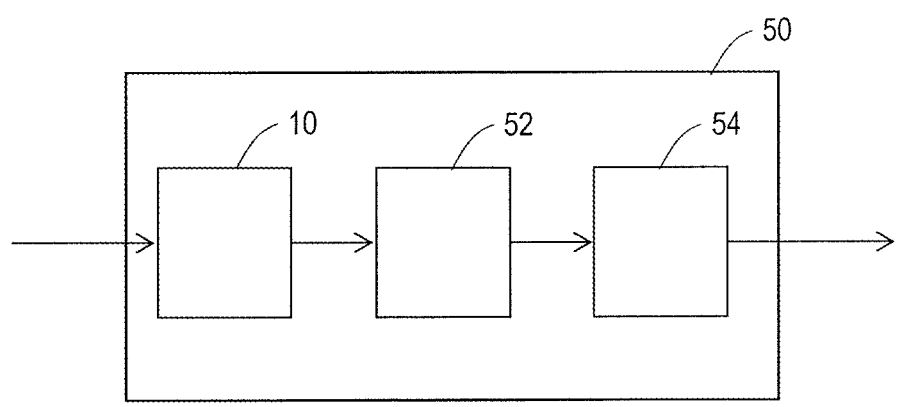
FIG. 10 A schematic diagram of an embodiment of an air cleaning device of the present invention.

Hereinafter, an embodiment of an air cleaning device 50 of the present invention is described with reference to FIG. 10.

The air cleaning device 50 of the present embodiment includes a catalyst-supporting film 10, an ion generating device 52, and a dust collection filter 54.

The ion generating device 52 generates a positive ion and a negative ion. The ion generating device 52 is, for example, a Plasmacluster ion (registered trademark) generating device which is manufactured by and commercially available from the applicant of the present application. The catalyst-supporting film 10 may be arranged in the form of a catalyst member 40 supported by the base 30. The dust collection filter 54 is preferably a HEPA filter. The HEPA filter is a type of air filter whose particle collection rate for particles of 0.3 µm in diameter at the rated flow rate is not less than 99.97% and whose initial pressure loss is not more than 245 Pa (Japanese Industrial Standards (JIS Standards)).

For example, air which is taken into the air cleaning device 50 is first supplied to the catalyst-supporting film 10. House dusts contained in the air are oxidatively degraded and deactivated by the catalyst-supporting film 10. The house dusts include pollens, spores, mites, mite droppings, and dead mite bodies. The diameter of cedar pollens is about 30 µm, and the diameters of pollens of other plants are approximately not less than 10 µm. Many of the other house dusts, such as mites, have sizes of not less than 2 µm and not more than 5 µm. The catalyst-supporting film 10 oxidatively degrades malodorous substances contained in the air to achieve deodorization.

Then, the Plasmacluster ion generating device 52 deactivates viruses and molds.

In the last, the dust collection filter 54 catches particles whose diameters are not more than 0.3 µm.

As described above, the air cleaning device 50 has not only a Plasmacluster ion generating function but also an oxidation function such that not only deactivation of viruses, and the like, but also deactivation of pollens and malodorous substances can be achieved. The catalyst-supporting film 10 is washable with water or alcohol, and therefore, maintenance of the catalyst-supporting film 10 is easy. Thus, the air cleaning device is applicable to a wider variety of uses.

The arrangement of the catalyst-supporting film 10 in the air cleaning device is not limited to the above-described example but may be appropriately varied according to the use or location of the air cleaning device. Further, the dust collection filter 54 may be omitted.

INDUSTRIAL APPLICABILITY

According to a catalyst-supporting porous film of the present invention, the catalytic action can be efficiently increased. Such a catalyst-supporting porous film is suitably used in an air cleaning device.

REFERENCE SIGNS LIST 10 catalyst-supporting porous film
12 resin layer
14 catalyst particles
22 porous section
24 supporting section
30 base
40 catalyst member
50 air cleaning device

The invention claimed is:
1. A catalyst-supporting porous film, comprising:
an exposed surface having a moth-eye structure or inverted moth-eye structure;
a resin layer;
a plurality of through holes arranged in a matrix; and
catalyst particles dispersed in the resin layer,
wherein the exposed surface includes the catalyst particles unevenly distributed such that substantially all of a surface of the resin layer is covered with the catalyst particles.

2. The catalyst-supporting porous film of claim 1, wherein the catalyst-supporting porous film includes a porous section and a supporting section for supporting the porous section, and
the number of catalyst particles per unit volume in the porous section is greater than the number of catalyst particles per unit volume in the supporting section.

3. The catalyst-supporting porous film of claim 1, wherein the surface has a plurality of minute raised portions and a saddle portion extending between vertexes of adjacent two of the plurality of minute raised portions.

4. The catalyst-supporting porous film of claim 1, wherein the resin layer contains a photocurable resin.

5. The catalyst-supporting porous film of claim 1, wherein the resin layer contains a plurality of thermoplastic resins which are phase-separated from one another.

6. The catalyst-supporting porous film of claim 1, wherein the catalyst particles include titanium oxide particles.

7. The catalyst-supporting porous film of claim 1, wherein the catalyst particles include zinc-supporting titanium oxide particles.

8. A catalyst member, comprising:
a base which has a principal surface; and
the catalyst-supporting porous film as set forth in claim 1 being provided on the principal surface of the base.

9. A catalyst member, comprising:
a base which has two principal surfaces; and
the catalyst-supporting porous film as set forth in claim 1 being provided on each of the two principal surfaces of the base.

10. An air cleaning device, comprising:
the catalyst-supporting porous film as set forth in claim 1; and
an ion generating device for generating a positive ion and a negative ion.

11. A manufacturing method of the catalyst-supporting porous film of claim 1, comprising the steps of:
providing a mixture which contains catalyst particles, a resin, and a solvent;
applying the mixture on a base and drying the mixture; and
deforming a surface of the dried mixture into a porous shape,
wherein the step of drying includes forming a resin layer from the mixture, in which the catalyst particles are dispersed, and
the catalyst particles are unevenly distributed so as to be present at a surface of the resin layer.

12. The manufacturing method of claim 11, wherein
in the step of providing, the resin contains a photocurable resin, and the step of deforming into the porous shape further includes curing the photocurable resin with a mold being pressed against the mixture.

13. The manufacturing method of claim 12, wherein in the step of curing, the mold has a surface of a moth-eye structure or inverted moth-eye structure.

* * * * *